United States Patent [19]
Collin et al.

[11] Patent Number: 5,656,672
[45] Date of Patent: Aug. 12, 1997

[54] WATER-IN-OIL EMULSION CONTAINING RETINOL ITS USE

[75] Inventors: Nathalie Collin, Sceaux; Eric Quemin, Villepinte, both of France

[73] Assignee: L'Oreal, Paris, France

[21] Appl. No.: 365,844

[22] Filed: Dec. 29, 1994

[30] Foreign Application Priority Data

Dec. 30, 1993 [FR] France ..................... 93-15862

[51] Int. Cl.$^6$ .................... A61K 31/07; A61K 31/695; A61K 31/045

[52] U.S. Cl. ................... 514/725; 514/63; 514/724; 514/859; 514/937; 514/938

[58] Field of Search .................. 514/724, 725, 514/63, 937, 938, 859

[56] References Cited

U.S. PATENT DOCUMENTS

| | | | |
|---|---|---|---|
| 4,333,924 | 6/1982 | Bowly et al. | 424/170 |
| 4,826,828 | 5/1989 | Wilmott et al. | 514/63 |
| 4,888,363 | 12/1989 | Dulak et al. | 514/725 |

FOREIGN PATENT DOCUMENTS

| | | |
|---|---|---|
| 0508848 | 10/1992 | European Pat. Off. . |
| 0 530 862 | 3/1993 | European Pat. Off. . |
| 2658739 | 8/1991 | France . |
| 2666308 | 3/1992 | France . |
| 2671055 | 7/1992 | France . |
| 9300085 | 1/1993 | WIPO . |

OTHER PUBLICATIONS

Chemical Abstracts. vol. 97 No. 11 ab. 98175m (1982) Bowley et al.

*Primary Examiner*—Kevin E. Weddington
*Attorney, Agent, or Firm*—Oblon, Spivak, McClelland, Maier & Neustadt, P.C.

[57] ABSTRACT

The invention relates to a water-in-oil emulsion containing retinol, an oil phase, an aqueous phase and an agent for emulsifying the aqueous phase in the oil phase, the oil phase containing at least one organic solvent for retinol which is liquid at room temperature, and the pH of the aqueous phase being basic, so as to stabilize the retinol for at least two months at 45° C.

This emulsion is for cosmetic or dermatological use.

29 Claims, 1 Drawing Sheet

WATER-IN-OIL EMULSION CONTAINING RETINOL ITS USE

BACKGROUND OF THE INVENTION

1. Field of the Invention

The present invention relates to a water-in-oil emulsion containing stabilized retinol, this emulsion being particularly intended for the cosmetic and/or dermatological fields. The invention also relates to a use of this emulsion for treating the skin and to packaging which is perfectly suitable for this emulsion.

2. Discussion of the Background

Retinol is known for its beneficial effects on the skin, in particular in topical application.

Retinol has for a long time been used in the treatment of acne. However, it is in the field of repair of damage caused either by age or by over-exposure to the sun that retinol has proven to be extremely active.

Thus, the effects of retinol on cell differentiation make it possible to envisage the use thereof for, inter alia, effectively combating the appearance of wrinkles and fine lines, and for combating dryness, roughness and/or stiffness of the skin. Its activity in the regeneration of tissues makes it a very important compound in cicatrization. Repeated application of cosmetic compositions containing retinol enables, inter alia, wrinkles to be removed, the skin to be rendered smooth and small cracks in the epidermis to be repaired.

On account of these beneficial effects, it has for a very long time been sought to formulate retinol in cosmetically acceptable compositions in a form which is stable for at least several months at room temperature.

An emulsion containing retinol, which may be used in cosmetics, is described in U.S. Pat. No. 4,826,828 and WO-A-93/00085.

U.S. Pat. No. 4,826,828 pertains to a water-in-oil emulsion containing retinol, a volatile silicone and a solvent for the retinol and the volatile silicones. The preferred solvent is ethanol. However, retinol is degraded in the presence of ethanol. In order to obtain the emulsion, U.S. Pat. No. 4,826,828 teaches the preparation of a solution containing retinol being mixed, into a water-in-oil emulsion, which is to be mixed at the time of use, in order to avoid any degradation thereof. In addition, the use of an antioxidant and a metal-chelating agent in the aqueous phase is indicated as being essential.

The stability of such compositions, as indicated on the packaging of products Bioadvance and Bioadvance 2000, does not exceed one month. Thus, the stability of retinol, in compositions of this type, is insufficient for prolonged use, which makes rapid reacquisition necessary, and is therefore expensive.

WO-A-93/00085 proposes stabilization of retinol in cosmetic compositions by addition to the latter of a stabilizing complex comprising, in combination, an antioxidant and a metal ion-chelating agent. However, although the stability of the retinol appears to be enhanced in such compositions (60% of the retinol still being present in the composition after storage for three months at 40° C.), the fact remains that the relative stability of the retinol is only due to the presence in the composition of a considerable amount of stabilizing antioxidants and chelating agents.

Much research has been carried out in order to minimize, or even to eliminate, the presence of such stabilizing agents in cosmetic compositions containing retinol, while at the same time retaining a stability thereof in the composition which is acceptable with regard to its effects and in relation with prolonged use of the composition.

It has been discovered, surprisingly and unexpectedly, that it is possible to formulate a water-in-oil emulsion containing retinol, that is stable with time and is intended for topical use, by appropriate selection of the various constituents of the emulsion, for the purpose of imparting specific physicochemical properties thereto.

SUMMARY OF THE INVENTION

The subject of the present invention is thus a water-in-oil emulsion comprising retinol, an oil phase and an aqueous phase, characterized in that the oil phase contains at least one organic solvent for retinol which is liquid at room temperature, and in that the pH of the aqueous phase is basic, so as to stabilize the retinol for at least 2 months.

The tests performed with an emulsion according to the invention showed a markedly improved retinol stability compared with that of the prior art.

The emulsion according to the invention has the advantage of still being able to contain 82% of active retinol after storage at 45° C. for 2 months.

The emulsion according to the invention is perfectly suitable for cosmetic and/or dermatological use.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
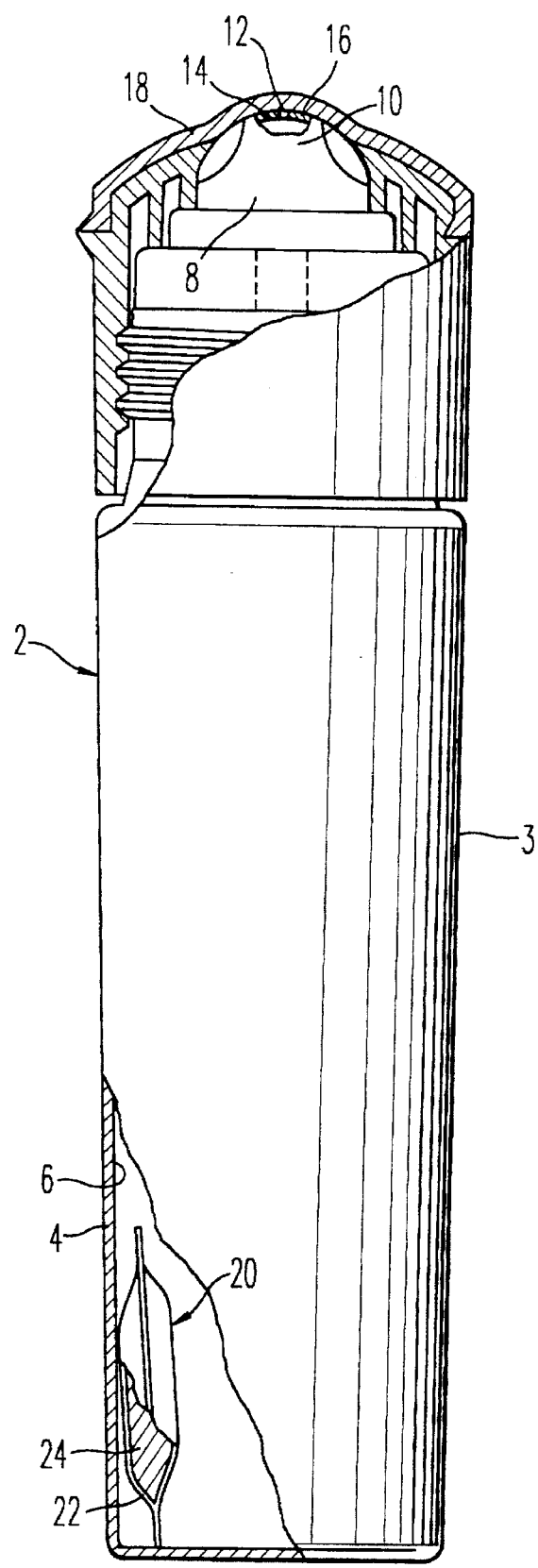
FIG. 1 provides a depiction of a package which is compatible with the emulsion of the present invention.

The proportions of the various constituents of the emulsion according to the invention are those that are conventionally used in the cosmetic or dermatological field and depend on the specific application envisaged.

In addition, in a preferred embodiment, the emulsion according to the invention is free of any metal ion-chelating agent and does not necessitate the use of an antioxidant.

In particular, the oil phase of the emulsion according to the invention may represent from 10% to 50% of the total weight of the emulsion and preferably from 20% to 35%.

Moreover, the aqueous phase of the emulsion according to the invention may represent from 50% to 90% of the total weight of the emulsion and preferably from 65% to 80%.

Retinol is generally present in the emulsion according to the invention in a proportion ranging from 0.001% to 10%, and preferably from 0.01% to 1%, of the total weight of the emulsion.

The retinol used in the emulsion according to the invention may be retinol in any of its conformations and in particular that in the all-trans form, such as that sold by the company Fluka under the name "all-trans-retinol". A characteristic feature of all-trans-retinol is that its retinol activity and its harmlessness are superior to those of other retinoids. Retinol may be prepared by conventional methods known to those of ordinary skill in the art (se U.S. Pat. No. 3,060,229).

The organic solvent for retinol may represent from 0.01% to 30% of the total weight of the emulsion according to the invention, and preferably from 0.1% to 10%.

The organic solvent, which is liquid at room temperature (at 20° C. for example), used in the invention may be any organic solvent that is capable of dissolving retinol, while at the same time retaining a good stability thereof. In particular, this solvent is chosen from the group consisting of $C_{16}$–$C_{20}$ branched-chain aliphatic fatty alcohols, $C_6$–$C_{14}$ dicarboxylic acid diesters of isopropyl alcohol, and $C_6$–$C_{18}$ fatty acid triglycerides and mixtures thereof.

Solvents of fatty alcohol type having a straight or branched chain, which is alkoxylated, destroy the stability of the emulsion according to the invention.

Among the $C_{16}$–$C_{20}$ aliphatic fatty alcohols which may be used in the invention, there may be mentioned 2-hexyldecanol such as that sold by the company Condea under the name "ISOFOL 16", octyldodecanol such as that sold by the company Henkel under the name "EUTANOL G", and isostearyl alcohol such as that sold by the company Sherex under the name "ADOL 66".

Among the $C_6$–$C_{14}$ dicarboxylic acid diesters of isopropyl alcohol which may be used in the invention, there may be mentioned diisopropyl adipate such as that sold by the company ISP under the name "CERAPHYL 230".

Among the $C_6$–$C_{18}$ fatty acid triglycerides according to the invention, mixed triglycerides of capric/caprylic acids such as those sold by the company Hüls France under the name "MIGLYOL 812" are preferably used.

In one particular embodiment of the invention, it is possible to use a mixture of two or more of these solvents for retinol.

Other conventional constituents of cosmetic, pharmaceutical or veterinary compositions may be introduced into the emulsions according to the invention. The nature of these ingredients and the proportion thereof should be compatible with the stability sought for the retinol in the emulsions according to the invention.

The oil phase of the emulsion according to the invention may contain an emulsifying agent that is capable of forming a water-in-oil emulsion and of withstanding basic pHs. In particular, this emulsifying agent is preferably a silicone-containing emulsifying agent, which is used in a proportion of from 0.5% to 10%, and preferably of from 1% to 6%, of the total weight of the emulsion. Among the emulsifying agents which may enter into the composition of the oil phase, there may be mentioned polyoxyethylenated $C_{10}$–$C_{22}$ alkyl dimethicone copolyols such as cetyl dimethicone copolyol or "ABIL EM-90" from the company Goldschmidt, or polyoxyethylenated and polyoxypropylenated lauryl dimethicone copolyol, for instance Q2-5200 from Dow Corning, and mixture of the two.

Polyoxyethylenated dimethicone copolyols such as SP 1228 from General Electric and also Q2-3225 C from Dow Corning may also be used.

The oil phase may also contain an additional oil other than the emulsifying agent, which is inert with respect to retinol, preferably chosen from mineral oils or silicone-containing oils.

Among the mineral oils which may be used according to the invention, isohexadecane, paraffin, isoparaffin and petrolatum may be mentioned among others.

Among the silicone-containing oils which may be used in the invention, dimethicones, dimethiconols, cyclomethicones such as cyclopentadimethylsiloxane (or cyclomethicone D5) or cyclohexadimethylsiloxane (or cyclomethicone D6) or alkyl dimethicones and a mixture of certain of these compounds, such as "GUM Q2-1401" from Dow Corning, may be mentioned among others.

The aqueous phase of the emulsion according to the invention has a basic pH above 8 and preferably ranging from 8.5 to 9.5. The pH of the aqueous phase is obtained by addition of any base which is compatible with the stability of the retinol to the emulsion according to the invention and in an amount which is acceptable suitable for obtaining the desired pH in the aqueous phase. Preferably, the base is acceptable for use either cosmetically, pharmaceutically or both. In practice, the base will be used in an amount ranging from 0.05% to 0.5% of the total weight of the emulsion.

Among the preference bases used in the invention, triethanolamine, aminomethylpropanol, aminomethylpropanediol, tris or aminomethylpropanetriol, sodium hydroxide, arginine, and lysine may be mentioned for example.

The emulsion according to the invention may additionally contain hydrophilic or lipophilic additives which are conventionally used in cosmetic or dermatological compositions.

Among the hydrophilic additives used in the emulsion according to the invention, moisturizing agents such as polyols (glycerol) and glycols may be mentioned.

Among the lipophilic additives, gelling agents such as bentone gel, for example that sold under the name "SIMA-GEL SI 345" by the company Biophil, and polyethylene waxes such as the polyethylene wax AC 617 from Allied Chemical may be mentioned.

The emulsion according to the invention advantageously contains stabilizing salts of non-metallic origin in a proportion, for example, of from 0.3% to 2% of the total weight of the emulsion, such as sodium chloride (NaCl) and potassium chloride (KCl).

The invention also relates to a use of an emulsion defined above for treating the skin, in particular for treating acne, and for treating damage caused by age and/or the sun.

The invention also relates to a process for preparing the emulsion according to the invention as defined above.

This preparation is carried out in an inert atmosphere (nitrogen or a noble gas such as helium., neon, argon, krypton and xenon) which is free of any oxygen, and in the presence of inactinic light such as that of a sodium vapor lamp.

The invention also relates to packaging which is suitable for the emulsion described above. This packaging is characterized in that it is provided with a dispensing device such that the product it contains is not brought into contact with the environment, in that it additionally contains an oxygen-trapping device and in that its walls are impermeable to gas or to visible-ultraviolet light. The product with this packaging is brought into contact with the environment only when it is used on the skin.

The dispensing device may consist of a valve or a pump which has no air intake, such as the device described in FR-A-2,666,308 or FR-A-2,658,739.

In one specific embodiment of the invention, the oxygen-trapping device is separated from the product contained in the packaging by a membrane which is gas-permeable and liquid-impermeable, especially to those liquids entering into the composition of the emulsion according to the invention.

The gas-permeable membrane may, for example, be that which is defined in FR-A-2,671,055.

Any means capable of absorbing oxygen without re-release may be used as oxygen-trapping device. For example, those devices sold by the company ATCO under the name "OXYGEN ABSORBER LH50" or "OXYGEN ABSORBER LH100, LH500" and others, may be mentioned.

The oxygen-trapping device which is isolated by the membrane may, in the packaging device, be integral or non-integral with the walls and submerged in the composition.

A general process for preparing the emulsions according to the invention will now be described. In a first step, the oil phase (A) and the aqueous phase (B) constituting the emulsion are prepared independently, and the aqueous phase (B) is then incorporated into the oil phase (A) with stirring at moderate speed on a Morits stirring apparatus at room temperature, under the normal conditions for preparing any water-in-oil emulsion. The mixture thus formed constitutes the emulsified support into which the retinol will be incorporated.

All of the components of the emulsion according to the invention are degassed under a nitrogen tent at room temperature, in a room lit by a sodium vapor lap, in order to remove all trace of oxygen and to replace the latter with nitrogen. This degassing takes place for at least two hours. When all trace of oxygen has been removed (this may be verified using an oxymeter), the retinol and its solvent are weighed and are mixed with magnetic stirring, until dissolution is complete, to form a phase (C). This phase (C) is then incorporated into the emulsion, stirring with a paddle to ensure good homogenization. Once complete, the emulsion is incorporated, still under an inert atmosphere of nitrogen and under sodium vapor light, into packaging as defined above.

Other features of the invention will become apparent in the course of the following descriptions of exemplary embodiments which are given for illustration of the invention and are not intended to be limiting thereof.

EXAMPLE 1
Cream for around the eyes

| A. Abil EM-90 | 2% |
|---|---|
| Cyclomethicone D5 | 7% |
| Simagel Si 345 | 5% |
| Miglyol 812 | 7.5% |
| Gum $Q^2$ 1401 | 4% |
| B. Glycerine | 5% |
| Triethanolamine | 0.2% |
| Deionized water | 61.3% |
| C. Isofol 16 | 7.5% |
| Retinol | 0.5% |

When applied around the eyes as a cure 2 to 5 times per week, this cream has a smoothing effect on the fine lines or "crow's feet" around the eye.

EXAMPLE 2
Anti-wrinkle cream

| A. Abil EM-90 | 3% |
|---|---|
| Cyclomethicone D5 | 7% |
| Simagel Si 345 | 5% |
| Miglyol 812 | 11.5% |
| Gum $Q^2$ 1401 | 3% |
| B. Glycerine | 5% |
| Triethanolamine | 0.2% |
| NaCl | 0.7% |
| Deionized water qs | 100% |
| C. Isofol 16 | 3% |
| Retinol | 0.18% |

This very soft and nourishing cream is ideal for daily application to the face, at night, for a long-term anti-wrinkle effect.

EXAMPLE 3
Anti-ageing body milk

| A. Abil EM-90 | 1% |
|---|---|
| Isolan Gi 34 | 5% |
| Liquid paraffin | 13% |
| Cyclomethicone D5 | 10% |
| Gum $Q^2$ 1401 | 4% |
| B. Glycerine | 5% |
| Triethanolamine | 0.2% |
| NaCl | 0.6% |
| Deionized water qs | 100% |
| C. Diisopropyl adipate | 1% |
| Retinol | 0.012% |

This supple body milk is excellent in the anti-aging care of the body provided that it is used daily on the whole body. After application, the skin is soft and smooth.

EXAMPLE 4
Care product for repairing the lips

| A. Abil EM-90 | 3% |
|---|---|
| Simagel Si 345 | 5% |
| Cyclomethicone | 7% |
| Gum $Q^2$-1401 | 3% |
| B. AMP | 0.12% |
| NaCl | 0.7% |
| Glycerine | 5% |
| Deionized water qs | 100% |
| C. Miglyol 812 | 11% |
| Retinol | 0.9% |

This compact cream, which slides very easily on application, constitutes a nourishing and repairing care product for damaged and wrinkled lips.

Furthermore, a stability test was performed in which an emulsion according to the invention (Example 1) was compared with various formulae derived from those of Example 1, (A, B, C, D, E, F).

Composition A

The oil phase of Example 1, to which the following are added:

| α-tocopherol | 0.1% |
|---|---|
| α-tocopherol acetate | 1% |
| ascorbyl palmitate | 0.2% | plus the aqueous phase of Example 1, to which is added:

| Dequest 2046[1] | 0.2% |
|---|---|

[1]pentasodium salt of 33% ethylenediaminetetramethylenephosphonic acid, as sold by the company Monsanto.

and in which the deionized water has been appropriately adjusted.

Composition B

The oil phase of Example 1, to which the following are added:

| Ascorbyl palmitate | 0.2% |
|---|---|
| 3-[(3,5-di-tert-butyl-4-hydroxy)-benzylidene) camphor | 0.5% | plus aqueous phase of composition A.

Composition C
The oil phase of Example 1 plus the aqueous phase of Example 1 from which the triethanolamine has been removed.

Composition D
The oil phase of the composition of Example 1 plus the aqueous phase of Example 1, plus phase C containing retinol dissolved Composition E
The oil phase of Example 1, to which has been added 0.5% of pure ethoxyquine (Raluquin from the company Raschig) plus the aqueous phase of Example 1.

Composition F
The composition of Example 1 into which the oxygen absorber isolated from the emulsion, is incorporated after manufacture.

The stability test for these compositions were carried out by measuring the percentage of degradation after storage for 1 month or 2 months, either at 4° C. or at room temperature or at 45° C. The results are given in the table below:

|  | 1 month | | | 2 months | | |
| --- | --- | --- | --- | --- | --- | --- |
| Compositions | 4° C. | Room Temp. | 45° C. | 4° | Room Temp. | 45° |
| 1 | 0 | 0 | 19 | 6 | 10 | 33 |
| A | 2 | 5 | 25 | 4 | 12 | 35 |
| B | 0 | 1 | 27 | 2 | 18 | 37 |
| C | 0 | 8 | 44 | 4 | 34 | 72 |
| D | 0 | 1 | 40 | 0 | 14 | 68 |
| E | 0 | 0 | 9 | 0 | 0 | 27 |
| F | 0 | 1 | 6 | 1 | 16 | 18 |

The results of these tests show that the emulsion according to the invention (Ex. 1,) has a retinol stability which is comparable with or even better than that containing one or more antioxidants (A, B) as described in the prior art, whereas emulsions prepared either with a retinol dissolved in a solvent other than those selected in the invention (D) or with a retinol in the presence of an aqueous phase at an unsuitable pH (C) are less stable. This table shows the possibility of stabilizing retinol in antioxidant-free emulsions, but also shows that the choice of a particular antioxidant (Raluquin, E) introduced into the emulsion according to the invention, may enhance the stability.

An example of packaging which is compatible with the emulsion according to the invention is described below, with reference to the attached figure (FIG. 1).

The packaging (2) is composed of a container, (3) the walls (4) of which are formed of any gas-impermeable material which may be made of, for example, a thermo-formed material or of any other suitable material wherein the internal surface of the walls, which is in contact with the emulsion (6), is non-metallic and that this material is impermeable to visible-ultra-violet rays.

The container (3) is surmounted by a dispensing device with no air intake (8) such as, for example, that which is described in document FR-A-2,666,308, consisting of a dome which is convex towards the outside (10) and of at least one slot (12) provided in the top of the dome.

The walls (14, 16) of the slot (12) are able to come into contact with each other in order to provide leaktight closing at rest. The device assemble (8) is surmounted by a hermetic cover (18) which provides double protection for the emulsion according to the invention contained in the packaging with regard to the environment.

A pocket (20) independent of the packaging, the walls (22) of which are formed of a gas-permeable and liquid impermeable membrane such as, for example, that described in document FR-A-2,671,055, contains an oxygen absorber (24). The encapsulated oxygen absorber (24) forms the oxygen-trapping device which is submerged in the emulsion according to the invention contained in the packaging device.

The membrane surrounding the oxygen-trapping device may be made of any material which is able to allow oxygen to pass through while at the same time remaining impermeable to liquids, in particular to the liquids constituting the emulsion according to the invention and, for example, is made of one of the materials chosen from polyethylene, polypropylene and polyethylene terephthalate.

When at rest, the walls (14,16) of the dome (10) are in close contact, thus providing the leak-tightness of the slot (12). By exerting a pressure on the packaging (2), a pressure is transmitted to the emulsion contained in this packaging, which will cause the walls (14,16) to separate, thereby enabling the emulsion to come out of the packaging. When the pressure is release, the walls (14,16) return to their rest position and seal the slot (12) closed.

Obviously, numerous modifications and variations of the present invention are possible in light of the above teachings. It is therefore to be understood that within the scope of the appended claims, the invention may be practiced otherwise than as specifically described herein.

This application is based on FR 93-15862, filed in France on Dec. 30, 1993, the entire contents of which are hereby incorporated by reference.

What is claimed as new and is desired to be secured by Letters Patent of the United States is:

1. A water-in-oil emulsion consisting essentially of:
   i) retinol;
   ii) an oil phase comprising at least one organic solvent for retinol, which is liquid at room temperature, and optional lipophilic additives, wherein said organic solvent is selected from the group consisting of $C_{16}$–$C_{20}$ branched-chain aliphatic fatty alcohols, $C_6$–$C_{14}$ dicarboxylic acid diesters of isopropyl alcohol, $C_6$–$C_{14}$ fatty acid triglycerides and a mixture thereof;
   iii) an aqueous phase containing water and optional hydrophilic additives; and
   iv) an agent for emulsifying the aqueous phase in the oil phase,
   wherein a pH of the said aqueous phase is basic.

2. The emulsion of claim 1, wherein the components of said emulsions are suitable for cosmetic or dermatological use.

3. The emulsion of claim 1, wherein said emulsion is free of any metal ion chelating agent.

4. The emulsion of claim 1, wherein said oil phase comprises from 10% to 50% of the total weight said the emulsion.

5. The emulsion of claim 1, wherein said oil phase comprises from 20% to 35% of the total weight of said emulsion.

6. The emulsion of claim 1, wherein said aqueous phase comprises from 50% to 90% of the total weight of said emulsion.

7. The emulsion of claim 1, wherein said aqueous phase comprises from 65% to 80% of the total weight of said emulsion.

8. The emulsion of claim 1, wherein said retinol is in an amount of from 0.001% to 10% of the total weight of said emulsion.

9. The emulsion of claim 1, wherein said retinol is in an amount of from 0.01% to 3% of the total weight of said emulsion.

10. The emulsion of claim 1, wherein said organic solvent is in an amount of from 0.01% to 30% of the total weight of said emulsion.

11. The emulsion of claim 1, wherein said organic solvent is in an amount of from 0.1% to 10% of the total weight of said emulsion.

12. The emulsion of claim 1, wherein said retinol is all-trans retinol.

13. The emulsion of claim 1, wherein said emulsifying agent is a silicone-containing emulsifying agent.

14. The emulsion of claim 1, wherein said emulsifying agent is in a proportion of from 0.5% to 10% of the total weight of said emulsion.

15. The emulsion of claim 1, wherein said emulsifying agent is in a proportion of from 1% to 6% of the total weight of said emulsion.

16. The emulsion of claim 1, wherein said emulsifying agent is selected from the group consisting of polyoxyethylenated $C_{10}$–$C_{22}$ alkyl dimethicone copolyols, polyoxypropylenated $C_{10}$–$C_{22}$ alkyl dimethicone copolyols, polyoxyethylenated and polyoxypropylenated $C_{10}$–$C_{22}$ alkyl dimethicone copolyols and a mixture thereof.

17. The emulsion of claim 1, wherein said oil phase further comprises an additional oil which is inert with respect to retinol.

18. The emulsion of claim 12, wherein said additional oil is selected from the group consisting of mineral oils and silicone-containing oils.

19. The emulsion of claim 17, wherein said oil is selected from the group consisting of isohexadecane, isoparaffin, petrolatum, paraffin, dimethicones, dimethiconols, cyclomethicones and alkyldimethicones.

20. The emulsion of claim 1, wherein said aqueous phase has a pH ranging from 8.5 to 9.5.

21. The emulsion of claim 1, wherein said aqueous phase further comprises a base selected from the group consisting of triethanolamine, aminomethylpropanol, aminomethylpropanediol, tris(aminomethylpropanetriol), sodium hydroxide, arginine and lysine.

22. The emulsion of claim 1, further comprising least one additive selected from the group consisting of polyols, glycols, stabilizing salts, Bentone gel, heavy or polyethylenated waxes, and petrolatum.

23. The emulsion of claim 1, further comprising at least one stabilizing salt in a proportion of from 0.3% to 2% of the total weight of said emulsion.

24. The emulsion of claim 23, wherein said stabilizing salt is a salt of a non-metal element.

25. The emulsion of claim 1, wherein said emulsion is packaged so as not to be in contact with oxygen or metal components, and so that it is protected from light.

26. A method for treating acne and for treating damage to the skin caused by age and/or the sun comprising topically applying the emulsion of claim 1, to skin in need thereof.

27. A process for preparing the emulsion of claim 1, wherein said emulsion is prepared under an atmosphere which is inert and free of any oxygen, and under inactinic light.

28. The process of claim 27, wherein said inert atmosphere consists of nitrogen or a noble gas.

29. The process of claim 27, wherein said oil phase and said aqueous phase are independently prepared, and said aqueous phase is incorporated into said oil phase, with subsequent addition of a phase-containing retinol and its solvent.

* * * * *